United States Patent [19]
Coffen et al.

[11] Patent Number: 5,061,629
[45] Date of Patent: Oct. 29, 1991

[54] PRODUCTION OF 2-HYDROXY SUBSTITUTED ARYLALKANOIC ACIDS AND ESTERS BY ENZYMATIC HYDROLYSIS

[75] Inventors: David L. Coffen, Glenridge; Panayiotis Kalaritis, New Providence; John J. Partridge, Upper Montclair, all of N.J.

[73] Assignee: Hoffman-La Roche Inc., Nutley, N.J.

[21] Appl. No.: 607,792

[22] Filed: Oct. 29, 1990

Related U.S. Application Data

[63] Continuation of Ser. No. 148,470, Jan. 26, 1988, abandoned.

[51] Int. Cl.$^5$ .......................... C07C 7/148; C12P 7/62; C12P 7/40
[52] U.S. Cl. .................................... 435/280; 435/135; 435/136; 435/874
[58] Field of Search ................ 435/135, 136, 280, 874

[56] References Cited

U.S. PATENT DOCUMENTS

| | | | |
|---|---|---|---|
| 4,668,628 | 5/1987 | Dahod et al. ........................ | 435/135 |
| 4,933,282 | 6/1990 | Hasegawa et al. ................... | 435/135 |
| 4,933,290 | 6/1990 | Cesti et al. ............................ | 435/280 |

FOREIGN PATENT DOCUMENTS 57-94295  6/1982  Japan .

OTHER PUBLICATIONS

J. Physiol., 30, 253 (1904).
J. Am. Chem. Soc., 77, 4271 (1955).
J. Am. Chem. Soc., 83, 4228 (1961).
Cambou and Klibanov, Applied Biochemistry and Biotechnology, vol. 9, pp. 255-260 (1984).
Kato et al., Tetrahedron Letters, vol. 28, No. 12, pp. 1303-1306 (1987).
Gu et al., Tetrahedron Letters, vol. 27, No. 43, pp. 5203-5206 (1986).
Dernoncour et al., Tetrahedron Letters, vol. 28, No. 40, pp. 4661-4664 (1987).
Kitazume et al., J. Org. Chem., vol. 51, pp. 1003-1004 (1986).
Xie et al., J. Chem. Soc., Chem. Commun., pp. 838-839 (1987).
Iriuchijima et al., "Asymmetric Hydrolysis of (±)-α-Substituted Carboxylic Acid Esters With Microorganisms," Agric. Biol. Chem., V45(6), 1389-1392, 1981.
Amano International Enzyme Co., Inc. Technical Bulletin, Lipase P.

*Primary Examiner*—Elizabeth C. Weimar
*Assistant Examiner*—Gail Poulos
*Attorney, Agent, or Firm*—George M. Gould; Bernard S. Leon; Alan P. Kass

[57] ABSTRACT

Enantiomerically pure (2R)-2-hydroxy arylalkanoic acid esters and (2S)-2-hydroxy arylalkanoic acids are prepared by the Pseudomonas lipase-catalyzed selective hydrolysis of racemic (2RS)-2-hydroxy arylalkanoic acid esters in solution or suspension in an aqueous medium at a controlled pH of from about 5 to about 9.

8 Claims, No Drawings

PRODUCTION OF 2-HYDROXY SUBSTITUTED ARYLALKANOIC ACIDS AND ESTERS BY ENZYMATIC HYDROLYSIS

This is a continuation of copending application Ser. No. 07/148,470 filed on Jan. 26, 1988 now abandoned.

BACKGROUND OF THE INVENTION

The specificity of certain microorganisms or of certain enzymes derived from microorganisms enables their potential use for the preparation of enantiomerically pure intermediates from racemic mixtures. The desired enantiomeric molecule can then be transformed into the target compound. Microorganism or enzyme-catalyzed resolution of isomers offers an attractive alternative to more traditional and costly methods, such as chemical resolution and high performance liquid chromatography of diastereomeric derivatives.

Kato et al. have reported that a known bacterium, *Corynbacterium equi* IFO 3730, has the ability to hydrolyze various esters enantioselectively (*Tetrahedron Letters*, Vol. 28, No. 12, 1987, pages 1303–1306). In their study, the microorganism was applied to the asymmetric hydrolysis of 2-benzyloxy substituted alkane- and arylalkane carboxylic acid esters, using a suspension of grown cells of *C. equi* and a prolonged (e.g., 24 hours) fermentation process. Unreacted lower alkyl esters were recovered in the optically active S-form in high enantiomeric excess (over 99% e.e.). It was also found that changing the alkyl or alkenyl moiety of the substrate with a phenylmethyl group caused a reversal of stereoselectivity, resulting in recovery of the optically active R-form, also in high enantiomeric excess.

Kitazume et al. have described a procedure for the asymmetric hydrolysis of 2-fluoro-2-methylmalonic acid diesters with pig liver esterase, giving the optically active (−)-2-fluoro-2-methylmalonic acid monoesters but with low enantiomeric excess. Also reported were the microbial hydrolysis of 2-fluoro-2-substituted malonic acid diesters with both esterase and cellulase to give the optically active (+)- or (−)-2-fluoro-2-substituted malonic acid monoesters (*J. Org. Chem.* 51, 1986, pages 1003–1006).

Gu et al. have reported that optically active 3-benzoylthio-2-methylpropionic acids can be prepared through the microbial lipase-catalyzed enantioselective hydrolysis of their corresponding esters. Enantio-selectivity to the desired sterochemically preferred S-isomer was poor with all lipases tried, necessitating structural changes in the aroylthio moiety of the substrate compound to achieve higher stereoselectivity. In particular, introduction of methoxy groups into the phenyl ring at the 3 and 5 positions resulted in improved stereospecificity using the lipase of *Mucor meihei*. (*Tetrahedron Letters*, Vol. 27, No. 43, 1986, pages 5203–5206).

Iuchijima et al. have described a process for the production of optically active 2-chloro- and 2-bromo-substituted alkyl esters and acids by the asymmetric hydrolysis of racemic mixtures of the ester, using the microorganisms Rizopus, Mucor, Aspergillus, Candida, Pseudomonas, Alcaligenes, Achromobacter and Bacillus, or enzymes derived from them. Published Japan Patent Application (Kokai) No. 57-94,295 (1982).

Also reported in the literature have been the Candida lipase-catalyzed enantioselective hydrolysis of racemic octyl 2-chloropropionate to the R-form of 2-chloropropionic acid (Cambou and Klibanov, *Appl. Biochem. Biotech*, 9, 1984, Page 255).

U.S. Pat. No. 4,668,628 (Dahod et al.) discloses a process for enzymatically resolving racemic mixtures of partially water-soluble esters, which involves contacting the racemic mixture with a Candida lipase enzyme to enzymatically hydrolyze it. A specific example is the Candida lipase catalyzed hydrolysis of D,L-methyl-2-chloropropionate.

A disadvantage of lipase-catalyzed kinetic resolutions in particular is that the specificity of the enzyme for a given substrate often cannot be anticipated in advance, since there is no useful model available for predicting the stereochemical outcome of a lipase-catalyzed kinetic resolution of a potential substrate.

SUMMARY OF THE INVENTION

This invention provides a novel process for obtaining optically pure (2R)-2-hydroxy arylalkanoic acid esters and (2S)-2-hydroxy arylalkanoic acids by the enzymatic kinetic resolution of racemic (2RS)-2-hydroxy arylalkanoic acid esters using a bacterial lipase enzyme.

More specifically, it has been discovered that this process can be used to convert the compound of formula I, below, into a mixture of the compounds of formulas IA and II, which can thereafter be separated to yield the desired 2R isomer of formula IA and the desired 2S isomer of formula II.

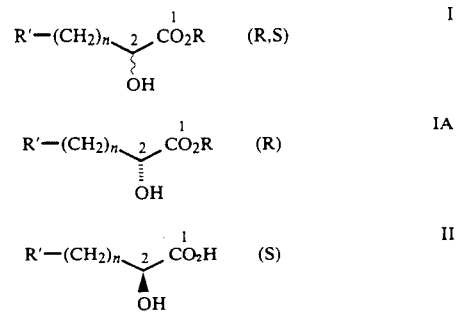

in which R' is aryl; R is alkyl, aryl or aralkyl, each of which can be unsubstituted or substituted; and n is zero or an integer from 1 to 8.

DETAILED DESCRIPTION OF THE INVENTION

As used throughout this disclosure, the term "alkyl" includes both straight and branched chain alkyl groups, preferably lower alkyl having from 1 to 8 carbon atoms, such as methyl, ethyl, propyl, isopropyl, butyl, and so forth.

As also used herein, the term "aryl" refers to mononuclear aromatic hydrocarbon groups such as phenyl, which can be unsubstituted or substituted in one or more positions, and polynuclear aryl groups such as naphthyl, anthryl, phenanthryl, and so forth, which can be unsubstituted or substituted with one or more groups. The preferred aryl groups are mononuclear aryl, especially phenyl.

The term "aralkyl" refers to straight and branched chain alkyl groups, preferably of 1 to 8 carbon atoms, terminating in an aryl group as described above.

Each of the above mentioned alkyl, aryl or aralkyl groups can optionally be substituted in one or more positions with a variety of substituents, such as halogen, alkoxy, aryloxy, thioalkoxy, thioaryloxy, and alkyl, preferably halogen (chloro, bromo, fluoro or iodo).

In the depiction of the compounds given throughout this description, a thickened taper line (▲) indicates a substituent which is in the beta-orientation (above the plane of the molecule, or page), a broken line (≡) indicates a substituent which is in the alpha-orientation (below the plane of the molecule, or page), and a wavy line ( ≀ ) indicates a substituent which is in either the alpha- or beta-orientation or mixtures of these isomers.

In accordance with this invention, it has been found that when the racemic mixture of formula I is subjected to enzymatic hydrolysis utilizing a bacterial lipase enzyme derived from a Pseudomonas species, the 2S-enantiomer of formula I is selectively hydrolyzed to produce the 2S-enantiomer of formula II. The enzymatic kinetic resolution can also be utilized to convert a racemic mixture of formula I to the 2R-enantiomer of formula IA.

This enzymatic hydrolysis thus produces the 2R-enantiomer of formula IA in admixture with the 2S-enantiomer of formula II. These compounds can be thereafter easily separated using conventional techniques.

In conducting the enzymatic resolution, the compound of formula I is dissolved or, if necessary, suspended in an aqueous medium. In suspending the compound of formula I in an aqueous medium, emulsifying agents may be used to enhance or to facilitate the emulsification, and conventional emulsifying agents may be utilized for this purpose.

The enzymatic hydrolysis is carried out at a pH of from about 5 to about 9, preferably at a pH of from about 6 to about 8. Any conventional method of maintaining the pH of the reaction mixture at the aforementioned pH can be employed. Among the preferred methods are the use of buffers or automatic titration.

In carrying out this enzymatic hydrolysis, the racemic mixture of formula I dissolved or otherwise dispersed in an aqueous medium is treated with a bacterial lipase enzyme. It is generally preferred to utilize the enzyme in a catalytically effective amount. As would be recognized, to achieve best results the choice of a particular catalytically effective amount of enzyme will depend upon factors within the control of one skilled in the art. These factors include the amount of starting material, the enzyme source, the unit activity of the enzyme, the purity of the enzyme, and so forth. An excess of a catalytically effective amount of the bacterial lipase enzyme can be used, but no additional beneficial results are obtained through the use of large excesses of enzyme.

As stated above, the enzymatic hydrolysis of the racemic mixture of formula I produces the isomer of formula IA in admixture with the compound of formula II. These compounds can be easily separated once the enzymatic hydrolysis is stopped, by immediate extraction of the reaction medium with a suitable organic solvent. Any conventional method of separation can be utilized to isolate the compound of formula IA form the compound of formula II. Among the conventional means for separating these two compounds are included extraction and distillation.

The compounds obtained by the method of this invention are useful as intermediates for the preparation of angiotensin converting enzyme (ACE) inhibitors which can be used to treat hypertension. Processes for the production of such ACE inhibitors from compounds such as involved here are known to those skilled in the art and described in the patent literature, including U.S. Pat. No. 4,474,694 (Oka et al.), U.S. Pat. No. 4,512,924 (Attwood et al.), U.S. Pat. No. 4,658,024 (Attwood et al.), and published European Patent Application No. 0 012 401 (Patchett et al.).

The present invention is further illustrated in the examples which follow, which are not intended to be limiting.

In these examples, the enantiomeric excess (% e.e.) is based on the diasteriomeric ratio of the derivatives of the ethyl (2R)- and (2S)-2-hydroxy-4-phenylbutanoates with S-(+)-α-methoxy-α-trifluoromethylphenylacetyl chloride (Mosher's reagent). The (2R)- and (2S)-2-hydroxy-4-phenylbutanoic acids were esterified in ethanol containing a catalytic amount of sulfuric acid at 2 hours of reflux, prior to derivatization. The derivatives with Mosher's reagent were prepared by stirring 2.4 mmoles of the substrate and 5.2 mmoles of Mosher's reagent in 2 mL of pyridine at 0° C. overnight. The diastereomeric ratio was determined by isothermal gas chromatography on a capillary OV-17 column at 225° C. See J. A. Dale et al., *J. Org. Chem.*, 36, 1969, p. 2543.

EXAMPLE 1

Preparation of Racemic 2-Hydroxy-4-Phenylbutanoic Acid

A 5 L three-neck flask equipped with a mechanical stirrer, a thermometer and a hydrogen adapter, was charged with 410.0 g of crude racemic 2-hydroxy-4-phenyl-3-butanoic acid, 2.5 L of methanol, and 3.4 g of a 1:1 5% Pd/C-water dispersion. Hydrogenation was conducted at 1 atm. and 20°-25° C. and was complete within 2 hours.

The reduction mixture was filtered through Hy-flo diatomaceous earth and the filtrate was concentrated at 45° C. under 70 mm Hg of vacuum, to give 412.0 g of crude 2-hydroxy-4-phenylbutanoic acid. The NMR spectrum of this crude acid was in agreement with its theoretical structure.

EXAMPLE 2

Preparation of Racemic Ethyl 2-Hydroxy-4-Phenylbutanoate

A 5 L three-neck flask equipped with a mechanical stirrer, a thermometer and a condenser, was charged with 412.0 g of crude racemic 2-hydroxy-4-phenyl-3-butanoic acid, 3 L of absolute ethanol, and 10 mL of concentrated sulfuric acid. The solution was heated at reflux for two hours, cooled to 23° C. and stirred at ambient temperature overnight. The solution was then carefully treated with 50 g of solid sodium bicarbonate and stirred for 10 minutes to neutralize the acid and to adjust the solution to pH 7. The resulting mixture was then dried over 50 g of anhydrous potassium carbonate and filtered. The solvent was evaporated at 45° C. and 70 mm Hg of vacuum to give 470.0 g of the crude ester, which was vacuum distilled 133°-134° C. and 1.5 mm Hg to give 310.0 g (65% yield) of ethyl 2-hydroxy-4-phenylbutanoate.

EXAMPLE 3

Enantioselective Hydrolysis of Racemic Ethyl 2-Hydroxy-4-Phenylbutanoate with Lipase Enzyme: Preparation of Ethyl (2R)-2-Hydroxy-4-Phenylbutanoate and (2S)-2-Hydroxy-4-Phenylbutanoic Acid

Method A: 50% Hydrolysis

A 3 L three-neck, round-bottom flask equipped with a mechanical stirrer, an electrode connected to a pH control unit and an addition tube connected to a peristaltic pump, was charged with 450 ml of deionized water, 50 ml of 0.05M aqueous phosphate buffer (pH 7.0) and 52.0 g of racemic ethyl 2-hydroxy-4-phenylbutanoate. The mixture was stirred for several minutes to make certain that the pH remained constant at 7.0. Then, 0.67 g (20,000 units) of Pseudomonas lipase enzyme (P-30, Amano International Enzyme Co., Inc., Troy, Va.) was added and the hydrolysis was allowed to proceed at pH 7.0 and room temperature, with stirring. The pH was kept constant by adding 1.0N aqueous sodium hydroxide solution via the peristaltic pump, which was activated by the pH control unit. The reaction was discontinued at 50% conversion when 125 ml of 1.0N aqueous sodium hydroxide solution had been added (at the 24 hour mark). The reaction mixture was then extracted with 3 portions of 200 ml (600 ml total) of diethyl ether. The combined organic layers were dried over anhydrous sodium sulfate and the solvent was removed at 45° C. under 70 mm Hg of vacuum, to provide 25.3 g of ethyl (2R)-2-hydroxy-4-phenylbutanoate (48.5% yield; 97% of theory), which was 91% enantiomerically pure $(\alpha)_D^{25}$ −7.8° (c 1.0, EtOH). The aqueous layer was acidified to pH 2 with 3N hydrochloric acid and extracted with 3×200 ml of diethyl ether. The combined organic layers were dried over anhydrous sodium sulfate and the solvent was removed at 45° C. and 70 mm Hg to give 20.8 g of (2S)-2-hydroxy-4-phenylbutanoic acid (46% yield; 92% of theory), which was 90.8% enantiomerically pure. $(\alpha)_D^{25}$ +7.6° (c 1.0, EtOH), m.p. 109°–110° C.

Method B: 55% Hydrolysis

A 3 L three-neck, round-bottom flask equipped with a mechanical stirrer, an electrode connected to a pH control unit and an addition tube connected to a peristaltic pump, was charged with 450 ml of deionized water, 50 ml of 0.05M aqueous phosphate buffer (pH 7.0) and 52.0 g of racemic ethyl 2-hydroxy-4-phenylbutanoate. The mixture was stirred for a few minutes to make certain that the pH remained constant at 7.0. Then, 1.0 g (30,000 units) of Pseudomonas lipase enzyme (P-30, Amano International) was added and the hydrolysis was allowed to proceed at pH 7.0 and room temperature, with stirring. The pH was kept constant by adding 1.0N aqueous sodium hydroxide solution via the paristaltic pump, which was activated by the pH control unit. The reaction was discontinued at 55% conversion when 137.5 ml of 1.0N aqueous sodium hydroxide solution had been added (at the 25 hour mark). The reaction mixture was then extracted with 3×200 ml (600 ml total) of diethyl ether. The combined organic layers were dried over anhydrous sodium sulfate and the solvent was removed at 45° C. under 70 mm Hg of vacuum to provide 22.4 g of ethyl (2R)-2-hydroxy-4-phenylbutanoate (43% yield; 96% of theory), which was 99% enantiomerically pure $(\alpha)_D^{25}$ −8.4° (c 1.15, EtOH). The aqueous layer was acidified to pH 2 with 3N hydrochloric acid and extracted with 3×200 ml of diethyl ether. The combined organic layers were dried over anhydrous sodium sulfate and the solvent was removed at 45° C. and 70 mm Hg to give 22.7 g of (2S)-2-hydroxy-4-phenylbutanoic acid (50% yield; 91% of theory), which was 73% enantiomerically pure. $(\alpha)_D^{25}$ +5.7°, m.p. 109°–110° C.

Method C: 35% Hydrolysis

The hydrolysis was repeated with the same hydroxy-substituted ester as previously, 0.34 g of Pseudomonas lipase enzyme (P-30, Amano International) 50 ml of 0.05M aqueous phosphate buffer (pH 7.0) and 450 ml of deionized water, under the same conditions as employed above. The reaction was stopped at 35% conversion when 85 ml of 1.0N aqueous sodium hydroxide had been added. Workup in standard fashion gave the following results:

|  | Ethyl (2R)-2-Hydroxy-4-Phenylbutanoate | (2S)-2-Hydroxy-4-Phenylbutanoic acid |
|---|---|---|
| Weight (g) | 32.5 | 14.6 |
| % Yield | 63 | 33 |
| % Theory | 96 | 93 |
| $(\alpha)_D^{25}$ | −4.6° (c 1.5, EtOH) | +7.8° (c 1.1. EtOH) |
| (% e.e.) | 52 | 92 |

We claim:

1. A process producing a 2R ester of the formula

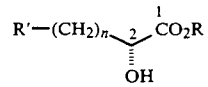

and for producing a 2S carboxylic acid of the formula

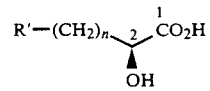

wherein R' is aryl, R is alkyl, aryl or aralkyl, each of which can be unsubstituted or substituted, and n is zero or an integer from 1 to 8;
comprising treating a racemic 2RS ester of the formula

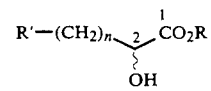

with Pseudomonas lipase P-30 enzyme in an aqueous medium to selectively convert the 2RS ester into the 2R ester and the 2S carboxylic acid, the treatment being carried out while the pH of the medium is maintained from about 5 to about 9, and thereafter recovering the 2R ester and the 2S acid separately from the medium.

2. The process of claim 1, wherein the aqueous medium is maintained at a pH of from about 6 to about 8.

3. The process of claim 1, wherein R' is phenyl.

4. The process of claim 3, wherein R is lower alkyl.

5. The process of claim 4, wherein R is ethyl.

6. The process of claim 1, for producing a compound of the formula

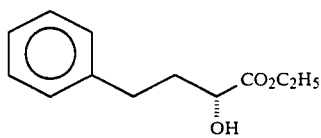

and a compound of the formula

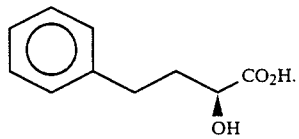

7. A process for producing a 2R ester of the formula

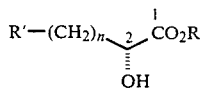

wherein R' is aryl, R is alkyl, aryl or aralkyl, each of which can be unsubstituted or substituted, and n is zero or an integer from 1 to 8, comprising treating a racemic 2RS ester of the formula

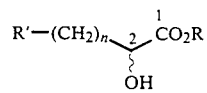

with Pseudomonas lipase P-30 enzyme in an aqueous medium to selectively convert the 2RS ester into the 2R ester, the treatment being carried out while the pH of the medium is maintained from about 5 to about 9, and thereafter recovering the 2R ester from the medium.

8. A process for producing a 2S carboxylic acid of the formula

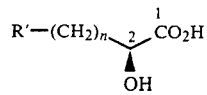

wherein R is aryl, R is alkyl, aryl or aralkyl, each of which can be unsubstituted or substituted, and n is zero or an integer from 1 to 8, comprising treating a racemic 2RS ester of the formula

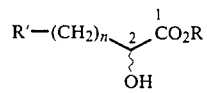

with Pseudomonas lipase P-30 enzyme in an aqueous medium to selectively convert the 2RS ester into the 2S carboxylic acid, the treatment being carried out while the pH of the medium is maintained from about 5 to about 9 and thereafter recovering the 2S carboxylic acid from the medium.

* * * * *